United States Patent [19]

Barron

[11] Patent Number: 4,671,936

[45] Date of Patent: Jun. 9, 1987

[54] ETHYLENE OXIDE STERILIZATION AND AERATION INDICATOR

[75] Inventor: William R. Barron, McKean, Pa.

[73] Assignee: American Sterilizer Company, Erie, Pa.

[21] Appl. No.: 454,585

[22] Filed: Dec. 30, 1982

[51] Int. Cl.[4] ........................ G01N 31/00; G01N 31/10
[52] U.S. Cl. .......................................... 422/55; 422/30;
   422/34; 422/57; 422/86; 436/1
[58] Field of Search ........................ 422/30, 34, 55, 56,
   422/57, 86; 436/1, 38, 93, 163; 210/94

[56] References Cited

U.S. PATENT DOCUMENTS

| | | | |
|---|---|---|---|
| 2,751,081 | 6/1956 | LaMotte | 210/94 |
| 3,851,043 | 11/1974 | Gunther | 422/30 |
| 3,992,154 | 11/1976 | Whithourne | 422/34 |
| 4,015,937 | 4/1977 | Miyamoto et al. | 422/55 X |
| 4,407,960 | 10/1983 | Trafnyek | 436/1 |
| 4,423,005 | 12/1983 | Murtaugh et al. | 436/1 |

Primary Examiner—Barry S. Richman
Assistant Examiner—William R. Johnson
Attorney, Agent, or Firm—Robert D. Yeager; Christine R. Ethridge

[57] ABSTRACT

Means are provided for the monitoring of a sterilization procedure employing alkylene oxide, particularly ethylene oxide, to sterilize medical equipment, especially heat-sensitive equipment, and especially for monitoring the aeration of the so-sterilized goods and articles to desorb the retained alkylene oxide, which means employ interaction of the alkylene oxide with a cation-exchange resin and subsequent aeration of the cation exchange resin coupled with pH indicator means sensitive to changes in the ion exchange resin effected by the alkylene oxide employed in the sterilization and subsequently by the air employed in the desorption step.

13 Claims, No Drawings

ETHYLENE OXIDE STERILIZATION AND AERATION INDICATOR

BACKGROUND OF THE INVENTION

Field of the Invention

A well established sterilization method employed by both hospitals and manufacturers of sterile goods employs an alkylene oxide, primarily ethylene or propylene oxide, of adjusted humidity, temperature, and concentration in an inert gas in an enclosed chamber to disinfect or sterilize especially heat-sensitive medical goods including, for example, medical and surgical instruments which are placed in the sterilizing chamber in packs, which constitute compact bundles of plastic or textile material to protect the instruments. A positive determination of the complete effectiveness of an alkylene oxide sterilization procedure can be determined by the kill factor of spores placed within the sterilization chamber during the process and subsequently cultured to determine the existence of any living microorganisms. This long and inconvenient procedure is routinely replaced by the placing of telltale indicators in the sterilization zone, which indicators by reaction with, for example, ethylene oxide indicate the presence of ethylene oxide, and, if properly buffered either physically or chemically, the presence of ethylene oxide for a sufficient period to ensure completed sterilization conditions.

Ethylene oxide while an efficient low temperature sterilant is an irritant that must be purged from the packs containing the articles being sterilized and from the articles themselves and this is routinely accomplished by an aeration procedure in which the sterilized goods are aerated in a chamber for a sufficient period to remove substantially all traces of the sterilant gas. The majority of sterilization indicators having reacted with the ethylene oxide to change color or to become colored are ineffective to monitor the subsequent aeration of the sterilized goods. Indicators which monitor the purging of ethylene oxide from medical goods in a sterilization method are disclosed in U.S. Pat. Nos. 3,738,811 and 3,992,154. The former patent discloses a method of frequent rupturing of an ampule and consequently permits only an approximation of the aerating cycle. The latter discloses a compound, 4(p-nitrobenzyl) pyridine which when suitably modified by other additives effects a color change by direct reaction with the ethylene oxide sterilant and then an additional color change by reaction of the resulting compound with air. A color changing indicator composition which relies upon changing the color of pH indicators for detecting the completion of sterilization by ethylene oxide but which is limited to monitoring solely the sterilization step and does not monitor the aeration procedure is disclosed in U.S. Pat. No. 4,015,937.

It is a primary object of this invention to provide a method and means for monitoring the alkylene-oxide sterilization and the subsequent aeration of medical goods, which means in part react first with the alkylene oxide to measure the sterilization process, and subsequently measure the aeration process, and in additional part include an indicator responsive to the result of aforesaid reactions which can be an altered potential or an alteration of the pH of the process to reflect, respectively, the completion of sterilization and aeration conditions.

It is a further object of the invention to provide a method of and means for monitoring the ethylene oxide sterilization of especially heat-sensitive medical goods and the subsequent desorption by aeration of the goods which method and means employ a strong acid cation exchange resin that will adsorb and react with the ethylene oxide and that subsequently will desorb the ethylene oxide (the aeration step) and an indicator means reflecting the result of said adsorption and subsequent desorption and so, by indicatorcolor change marking respectively the completion of sterilization and of aeration of the said goods.

SUMMARY OF THE INVENTION

A comminuted strong-acid cation exchange resin supported on a filter paper, a plastic tape or other backing, contained within an envelope, or pressed into a pellet is coated or intimately mixed with a pH indicator, of which a preferred indicator is Quinidine red. If an envelope is employed, one face thereof will be transparent and another selected to permit a gradual passage therethrough of ambient gas. The coated resin is placed into a sterilization chamber along with the medical goods to be sterilized. As ethylene oxide, diluted with an inert gas and of adjusted relative humidity, temperature and pressure, is pressured into the chamber, the ethylene oxide will come into contact with the medical goods and sterilize them by reaction with the microorganisms contained thereon and into contact also with the coated cation exchange resin. Reaction of the ethylene oxide with the resin will effect an increase in the pH of the moist resin surface and cause the pH indicator to change color, in the case of Quinidine red, to a bright red. With completion of sterilization being thus indicated, the sterilized medical goods are removed from the sterilizer and then placed in an aeration chamber along with the cation resin indicator device. Completion of aeration (desorption of the ethylene oxide from the medical goods) which may take from 10 to 24 hours will then be indicated by a return of the cation exchange resin to substantially its original uncolored, or off-white form.

It is at present usual practice in the operation of sterilizers to discharge residual ethylene oxide from the sterilization chamber and then to open the chamber and remove the sterilized packs. At this time the indicator of invention can be examined for the appropriate color change. Subsequently the sterilized packs are placed in an aerator along with the indicator and after some hours of aeration of the pack, frequently overnight, the packs purged of all residual ethylene oxide are removed for use. An improved procedure contemplates the aeration of the sterilized packs in the sterilization chamber by total displacement of the ethylene oxide with air pumped into the chamber and allowed to escape therefrom. In this case the telltale indicator of invention can be quickly examined to ensure total sterilization and then be allowed to remain with the packs during aeration, or means can be employed utilizing the change in potential of an ion exchange resin membrane cell to indicate on an external dial of a voltmeter the completion of the sterilization and aeration cycles.

There are readily available numerous published lists of synthetic acid base indicators (see for example, Hackh's Chemical Dictionary, pages 436, 437, and 438, 1944 edition) from which can be selected an indicator which will change color coincident with the total disinfection by ethylene oxide of the packs being sterilized.

Preferably a pH indicator should be used which changes color between pH's of 0 and 3. Other criteria can also be employed in the selection of an appropriate indicator; for example, an indicator should be selected which is not affected by the diluent of the ethylene oxide.

Preferred cation exchange resins for use in the method and means of invention are recited in U.S. Pat. No. 3,851,043 which discloses and claims a method of stripping ethylene oxide from the exhaust gas of a sterilizer using a strong acid cation-active ion exchange resin in the hydrogen form in bulk but which does not recognize the potentialities of these resins as a component of a monitoring system. The resins of the cation active type contain sulfonic acid functional groups in the polymer matrix and can be prepared by the nuclear sulfonation of styrenedivinylbenzene. Resins of this type are sold by Rohm and Haas Company under the trade designations IR 120, IR 121, IR 122 and IR 200; by Diamond Alkali under the trade designations C20 and C25; and by Nalco under the trade designations HCR, HGR and HDR. These resins are employed, and are commercially available, in comminuted form. Preferably the resins are screened to pass through a 40 and remain on a 60 mesh standard screen. The resin can also be pressed into tablet form or be incorporated in a membrane. A tablet can then be dyed with one of the selected pH indicators. The factors determining the total efficacy of ethylene oxide sterilization such as concentration of the ethylene oxide in the sterilant gas, the temperature of the gas, the controlled relative humidity of the gas, and the nature of the medical goods being sterilized are well-known and can be standardized and checked against the above-mentioned positive determination of complete sterilization by the spore generation method. The ion exchange resin its coating or intimate admixture ("dyeing") with a pH indicator, its support on a paper or film and the porosity of an envelope containing the resin can all be readily reflected to cause the color change to coincide with total sterilization plus a selected safety factor. The following specific examples compare variations in the following preferred mode of employing the method and means of the present invention.

EXAMPLE 1

A Dowex HCR-W-H strong-acid cation exchange resin of the hydrogen form is powdered in a mortar and screened to between 40 and 60 mesh standard sieves. The resin is then dyed with Quinidine red producing a powder of a light yellow coloration and this powder is packaged in small increments in a Bard Peel Pak. The Peel Pak was then placed in an ethylene oxide sterilizer of the brand Medallion of American Sterilizer Company, the ethylene oxide being diluted with dichlorodifluoromethane the concentration of the ethylene oxide in the sterilizer being about 600 milligrams per liter. The pressure in the sterilizer is at about eight pounds per square inch gauge and the controlled moisture level (relative humidity) therein is substantially above 50 percent. After exposure of the medical goods to the ethylene oxide for a period of one hour and forty-five minutes, the dyed or coated powder turned brilliant red. The medical goods were then removed and placed in an aeration chamber. After seven days of aeration with air at ambient room temperature, the packaged powder in the Peel Pak had returned to its original near yellow color.

EXAMPLE 2

In another example in which the same sterilization was completed as indicated by the same composition of powdered resin and Quinidine red, aeration of the sterilized goods was performed for five hours at ambient temperature and for 15 hours at 50° C. The indicator was restored to its original yellow color.

EXAMPLE 3

Sterilization was performed in the same manner as in Example 1 with another portion of the same packaged powder in the Bard Peel Pak and the medical goods with associated indicator package were aerated for a period of 20 hours with heated air at which time the powder was restored to its original yellow color thus suggesting by comparison with Example 2 that for at least the first few hours of aeration the employed air does not have to be heated to accelerate the desorption of ethylene oxide from the goods.

EXAMPLE 4

The procedure of Example 1 was followed with the exception that a silica gel adsorbent was added to the cation-ion exchange resin composition to determine whether the phenomenon was primarily only a matter of merely absorption of the ethylene oxide and whether the presence of silica gel would interfere with the interaction of the ethylene oxide with the cation exchange resin. The addition of the silica gel had no substantial effect on the results above indicated for Example 1 except possibly the results of color change and restoration of original color were not quite as pronounced.

EXAMPLE 5

In furtherance of this study to determine that the effect being measured is that of adsorption and interaction of the ethylene oxide on and with the cation exchange resin and the restoration of the original color by aeration of the ethylene oxide-ion exchange resin complex and not simply a reaction of the ethylene oxide with the pH indicator, silica gel and talc were mixed and dyed with Quinidine red. The product was exposed to ethylene oxide in a Porta Gas Sterilizer, a product of American Sterilizer Company, for three hours and an ethylene oxide concentration of 680 milligrams per liter, a period of concentration known to sterilize medical goods subjected to such conditions. There was no change in color of the dyed powder, thus demonstrating that the change in color in the Quinidine red is not caused by its reaction with ethylene oxide.

EXAMPLE 6

The pH indicator Para Rosaniline-HCL was used to dye both silica gel and talc and these powders were separately exposed in the Porta Gas Sterilizer to ethylene oxide in a concentration of 680 milligrams per liter for three hours. Here again there was no pronounced change to indicate any reaction of the ethylene oxide with the Para Rosaniline-HCL although in the case of the latter on talc some dilution of the original reddish-purple color to lavender was observed.

EXAMPLES 7 and 8

Two pellets consisting in one instance of molded, comminuted Quinidine-red-dyed ion exchange resin and in the other of molded comminuted Quinidine-red-dyed ion exchange resin plus silica gel, were prepared and exposed to ethylene oxide in an inert gas in a concentration of about 320 milligrams per liter in a Medallion sterilizer for a period of one hour and forty-five minutes. The pellets, packaged in a Bard Peel Pak consisted in one instance (Example 7) of the resin dyed with Quinidine red solution and alcohol and in another (Example 8) of the dyed resin and silica gel. The separate pellet was then placed with the sterilized goods in an oven at 50° C. for aeration. The pellets were examined at the below indicated intervals to determine their effectiveness in indicating the completion of aeration. The results are given below in Table 1 and indicate that while inclusion with the pellets of silica gel does not appear to be necessary in indicating the completion of sterilization and in fact interferes somewhat in the formation of the brillant red color of the indicator Quinidine red, in this case of using pellets instead of powder or membrane, the absorbent silica gel aided in accelerating the return of the ion exchange resin pellet to its original color. It is clear then when pellets are employed that the inclusion with the ion exchange resin of the silica gel absorbent in selected proportion will effect an adjustment of the rate of color change so as to make the same coincide with completion of sterilization.

TABLE 1

Aeration Monitored By Pellets

| Time After Sterilization | Dyed Resin Only | Dyed Resin And Silica Gel |
|---|---|---|
| 0 hr. | brilliant red | splotchy red |
| 1 hr. | red-red pink | faded pink |
| 2 hr. | pink | badly faded little color left |
| 3.5 hr. | orange pink edges of pellet starting to crumble | pellet crumbled and/or nearly nearly gone |
| 4.5 hr. | orange pink original color pellet crumbles | pale yellow original color at 5.5 hr. |
| 6 hr. | orange pink | |
| 21 hr. (overnight) | very, very light orange almost original color | |

EXAMPLES 9 to 16

Dichlorodifluoromethane is an inert diluent typically utilized in sterilization procedures using ethylene oxide. In order to determine whether this diluent masks or otherwise alters the monitoring of the sterilization and aeration processes, powder consisting of cation exchange resin dyed with Quinidine red were packaged in Bard Peel Paks and were also formed into two disks. One of each of the disks and packaged powders were placed in a sterilization chamber into which was introduced 100% ethylene oxide in one instance, (Examples 9 and 10) and 100% ethylene oxide and accompanying humidity in another (Examples 11 and 12) and held at room temperature. In both instances there was an almost immediate change in color to brillant red, the disk being only somewhat slower, the red coloration stating at the edge of the disk and progressing inward (a chromatographic effect available for measuring rate of sterilization) until the whole sample was red in approximately thirty minutes. The disks and packages were then put in an aerator at 52° C. and held therein overnight; the color of both the disks and the packaged powder had disappeared.

Another of the so prepared disks and packaged powder were placed in the sterilizer and exposed to 100% of the dichlorodifluoromethane (Examples 13 and 14) and in another test to 100% of the dichlorodifluoromethane and accompanying moisture (Examples 15 and 16). The diluent gas, dichlorodifluoromethane, causes no color change in the disk or packaged powder with or without accompanying moisture.

EXAMPLE 17

An cation exchange resin IR 120 +H, a resin of the amber type manufactured by Rohm and Haas Company was ground and screened to pass a 40 and remain on a 60 standard mesh screen. Twenty five cc of the above-screened resin was dyed with ten milliliters of a twenty-five percent weight per volume of Quinidine red solution in denatured ethanol. The dyed moist resin was then added to about 60 cc of denatured alcohol and was subsequently stirred with distilled water allowed to set for thirty minutes, decanted, washed again and filtered on a 100 mesh stainless steel screen and dried at 45° C. This carefully prepared cation exchange resin powder was packaged and then placed in a Medallion sterilizer and subjected to sterilizing gas consisting of 654 mg. per liter of ethylene oxide and controlled relative humidity for a period of 1 ¾ hour. There was a precise and strong color change to brillant red. The sterilization process was repeated employing a concentration of ethylene oxide of 326 milligrams per liter for the same period of 1 ¾ hour after which some color change was observed, indicating that with careful, standardized preparation of the dyed cation exchange resin, a quantitative measurement of the concentration of the sterilizing gas can be estimated from an observation of the rate and extent of color change.

EXAMPLE 18

A further sample of the powdered cation exchange resin prepared as in Example 17 was placed in a Bard Peel Pak and after sterilization of accompanying medical goods was observed by the change of the indicator to brillant red, the medical goods and sample were aerated at 50° C. for a period of 3 ½ hours whereupon a change back to the original color was noted. This period of aeration at the given temperature of 50° C. appears to be near the limiting value of aeration time as a repeat of this example did eliminate the brillant red but left a slight pink color.

EXAMPLE 19

A pliable plastic disk containing the comminuted cation exchange resin that is dyed as described in the foregoing Example 17 was made by mixing two grams of the said resin with two grams of Geon 121 (a polyvinyl chloride or chloroethylene polymer), 1.5 grams of dioctyl phthalate and 0.6 grams of glycerine. This mixture was cured for three minutes at 171° C. The resulting pliable plastic disk, when placed in a Medallion sterilizer and subjected to an ethylene oxide sterilization cycle for a period of 1 ¾ hours displayed a good color change on the edges of the disk, even though the center was somewhat splotchy. Aeration also would require considerably longer than 3 ½ hours to effect a color reversal. Such pliable plastic disks are in convenient form for marketing and storage for future use, preferably in opaque envelopes. While markedly less sensitive to aeration than packaged powder, such disks will incorporate per se a safety factor ensuring complete removal from sterilized goods of ethylene oxide.

EXAMPLE 20

Dyed cation exchange resin prepared as in Example 17 was applied to tape in admixture with a moisture absorbent, in one example 10% weight per volume of glycerine and in another Permasorb, a desiccant, and a product of Superior Valve Company of Washington, Pa. The respective tapes were placed in a Medallion sterilizer and exposed to a standard Medallion cycle, the ethylene oxide being in a concentration of 654 mg. per liter, for 1 ¾ hours. A good color change to brilliant red was observed in both instances. Upon aeration at 50° C., both of the tapes reverted to the yellowish original color in 2 ½ hours, too rapid to coordinate with complete aeration of ethylene oxide sterilized medical goods, thus calling for modification of the resin coating on the tape by, for example, the addition of an adjusted fractional part of the formulation of Example 19.

EXAMPLES 21, 22, 23 and 24

Four small Bard Peel Paks were prepared containing powder respectively identical to the cation exchange powder of Examples 18, 19 and 20 plus the dyed cation exchange powder of Example 18 ground with dioctyl phthalate and processed at 130° F. All four of the Peel Paks were then subjected to the conditions of sterilization of medical goods in a Medallion sterilizer employing a standard sterilization cycle of 1 ¾ hours and a concentration of ethylene oxide of 654 milligrams per liter. Subsequent to the sterilization cycle two post-sterilization vacuum pulses were employed to remove the major portion of residual ethylene oxide. Each of the four Bard Peel Paks were then subjected to aeration at 50° C. for the periods of 1 hour, 2 hours, 6 hours and 20 hours or before. Everyone of the samples retained the red color through the first two hours of aeration and change to a lighter red after six hours. At the end of the twenty hours period all of the packaged powders has turned to the original yellow color.

The conditions of Example 17 were repeated using numerous other pH indicators, namely Erythrosin B, 4 phenylazodiphenyl amine and Metanil yellow. These agents underwent their usual pH color change as ethylene oxide in the sterilizing gas became adsorbed on a strong acid cation exchange resin thereby increasing the pH of the surface of the resin in intimate contact with the pH indicator.

Unused indicator packages of comminuted resin such as those which were employed, for example, in Example 3 were placed in a desiccator and treated with moist air for four days. There was no change in the original yellow color of the dyed powder thus demonstrating the stability of the cation exchange resin and applied pH indicator. If, however, either packaged powder or disks have been exposed to ethylene oxide in a sterilization step and have been subsequently aerated so as return to their original color or absence thereof, and if they are to be stored for future checking, a wet humid atmosphere is to be avoided as it has been found that moisture can affect the color of the stored aerated samples.

What is claimed is:

1. Means for monitoring and determining the effective end point of sterilization conditions in which an alkylene oxide is employed to sterilize in a sterilization chamber medical goods and articles including packs containing surgical instruments, and for monitoring and determining the effective end point of a process of aeration of so-sterilized goods and articles to desorb the same of the alkylene oxide, said means consisting essentially of a strong acid cation exhange resin in a discrete form suitable for inclusion with the goods during sterilization and aeration and a color changing pH indicator means associated with the said discrete form of cation exchange resins;

said cation resin and said ph indicator means undergoing a two step reaction to monitor and determine the effective end point of sterilization wherein said cation exchange resin reacts with the alkylene oxide to effect a change in the pH of said cation exchange resin and said of pH of indicator means registers such change by displaying a distinct color response visible to the naked eye; and said cation exchange resin and said pH indicator means being suitable for subsequently monitoring the effectiveness of the aeration process wherein said cation exchange resin undergoes an additional change which effects a reversion of the pH indicator means to its original precolored state.

2. The means of claim 1 in which the alkylene oxide is ethylene oxide and the cation exchange resin is in the discrete form of a gas permeable package of small, predetermined sized particles of a strong acid synthetic cation exchange resin which has been dyed with a selected pH indicator that changes color to reflect that reduction in hydrogen ion concentration on the surface of the said resin which is effected by the ethylene oxide adsorbed on and reacted with the said surface during ethylene oxide sterilization and that subsequently reverts to its original color to reflect the alteration of the surface of the said resin effected by air employed in desorbing the goods being sterilized of residual ethylene oxide.

3. Means for monitoring and determining the effective end point of sterilization conditions in which ethylene oxide is employed to sterilize in a sterilization chamber medical goods and articles including packs containing surgical instruments, and for monitoring and determining the effective end point of a process of aeration of so-sterilized goods and articles to desorb the same of the ethylene oxide, said means consisting essentially of a powdered strong acid cation exchange resin of small predetermined sized particles in a gas permeable, at least oartially transparent envelope suitable for inclusion with the goods during sterilization and aeration and a color changing pH indicator means deposited on the surface of the said cation exchange resin, said envelope permitting (1) penetration of ethylene oxide and of air when placed respectively in a sterilization zone and a subsequently an aeration zone and (2) visual inspection upon termination of said sterilization and said aeration;

said cation exchange resin and said pH indicator means undergoing a two step reaction to monitor and determine the effective end point of sterilization wherein said cation exchange resin reacts with the ethylene oxide to effect a reduction in hydrogen ion concentration on the surface of said cation exchange resin to change the pH of said cation exchange resin and said pH indicator means registers such change by displaying a distinct color response visible to the naked eye; and said cation exchange resin and said pH indicator means being suitable for subsequently monitoring the effectiveness of the aeration process wherein said cation exchange resin undergoes an additional change which effects a reversion of the pH indicator means to its original precolored state.

4. Means for monitoring and determining the effective end point of sterilization conditions in which an alkylene oxide is employed to sterilize in a sterilization chamber medical goods and articles including packs containing surgical instruments, and for monitoring and determining the effective end point of a process of aeration of so-sterilized goods and articles to desorb the same of the alkylene oxide, said means consisting essentially of a powdered strong acid cation exchange resin suoported upon a substrate consisting of a plastic or cellulosic film suitable for inclusion with the goods during sterilization and aeration and a color changing pH indicator means associated with the said cation exchange resin;

said cation exchange resin and said pH indicator means undergoing a two step reaction to monitor and determine the effective end point of sterilization wherein said cation exchange resin reacts with the alkylene oxide to effect a change in the pH of said cation exchange resin and said nH indicator means registers such change by displaying a distinct color response visible to the naked eye; and said cation exchange resin and said pH indicator means being suitable for subsequently monitoring the effectiveness of the aeration process wherein said cation exchange resin undergoes an additional change which effects a reversion of the pH indicator means to its original precolored state.

5. Means for monitoring and determining the effective end point of sterilization conditions in which an alkylene oxide is employed to sterilize in a sterilization chamber medical goods and articles including packs containing surgical instruments, and for monitoring and determining the effective end point of a process of aeration of so-sterilized goods and articles to desorb the same of the alkylene oxide, said means consisting essentially of a strong acid cation exchange resin in a comminuted from and incorporated in a thermoplastic resin composition so as to form a flexible transparent plastic disk suitable for inclusion with the goods during sterilization and aeration and a color changing pH indicator means associated with the said cation exchange resin;

said cation exchange resin and said pH indicator means undergoing a two step reaction to monitor and determine the effective end point of sterilization wherein said cation exchange resin reacts with the alkylene oxide to effect a change in the pH of said cation exchange resin and said pH indicator means registers such change by displaying a distinct color response visible to the naked eye; and said cation exchange resin and said pH indicator means being suitable for subsequently monitoring the effectiveness of the aeration process wherein said cation exchange resin undergoes an additional change which effects a reversion of the pH indicator means to its original precolored state.

6. The means of claim 5 in which the flexible transparent plastic disk consists of a composition cured at high temperature comprising a modified chlorethylene polymer.

7. Means for monitoring and determining the effective end point of sterilization conditions in which an alkylene oxide is employed to sterilize in a sterilization chamber medical goods and articles including packs containing surgical instruments, and for monitoring and determining the effective end point of a process of aeration of so-sterilized goods and articles to desorb the same of the alkylene oxide, said means consisting essentially of a strong acid cation exchange resin in a pellet from of compressed comminuted exchange resin suitable for inclusion with the goods during sterilization and aeration and a color changing pH indicator means associated with the said pellet form of cation exchange resin;

said cation exchange resin and said pH indicator means undergoing a two step reaction to monitor and determine the effective end point of sterilization wherein said cation exchange resin reacts with the alkylene oxide to effect a change in the pH of said cation exchange resin and said pH indicator means registers such change by displaying a distinct color response visible to the naked eye; and said cation exchange resin and said pH indicator means being suitable for subsequently monitoring the effectiveness of the aeration process wherein said cation exchange resin undergoes an additional change which effects a reversion of the pH indicator means to its original precolored state.

8. The means of claim 7 in which the cation exchange resin is in admixture with an absorbent.

9. The means of claim 8 in which the absorbent is silica gel.

10. The means of claim 3, 4, or 5 in which the pH indicator is Quinidine red.

11. The means of claim 3, 4, or 5 in which the pH indicator is 4 phenylazodiphenylamine.

12. The means of claim 3, 4, or 5 in which the pH indicator is Metanil yellow.

13. The means of claim 3, 4, or 5 in which the pH indicator is Erythrosin B.

* * * * *

UNITED STATES PATENT AND TRADEMARK OFFICE
CERTIFICATE OF CORRECTION

PATENT NO. : 4,671,936
DATED : June 9, 1987
INVENTOR(S) : William R. Barron

It is certified that error appears in the above—identified patent and that said Letters Patent is hereby corrected as shown below:

Col. 5, line 61, delete "stating" and substitute therefor --starting--.
Col. 8, line 9, before "resin" insert --exchange--.
Col. 8, line 9, delete "ph" and substitute therefor --pH--.
Col. 8, line 14, delete "of" in both occurrences.
Col. 8, line 47, delete "oartially" and substitute therefor --partially--.
Col. 9, line 12, delete "suoported" and substitute therefor "supported".
Col. 9, line 22, delete "nH" and substitute therefor "pH--.
Col. 9, line 42, delete "from" and substitute therefor --form--.
Col. 10, line 45, delete "3, 4, or 5" and substitute therefor --3, 4, 5 or 7--.
Col. 10, line 47, delete "3, 4, or 5" and substitute therefor --3, 4, 5 or 7--.
Col. 10, line 48, "4" should not be in bold type.
Col. 10, line 49, delete "3, 4, or 5" and substitute therefor --3, 4, 5 or 7--.
Col. 10, line 51, delete "3, 4 therefor --3, 4, 5 or 7--.

Signed and Sealed this

Second Day of February, 1988

Attest:

DONALD J. QUIGG

Attesting Officer

Commissioner of Patents and Trademarks